United States Patent
Gupte et al.

(10) Patent No.: US 7,410,634 B2
(45) Date of Patent: Aug. 12, 2008

(54) TISSUE METABOLIC STRESS MONITORING

(75) Inventors: Pradeep M. Gupte, Airmont, NY (US); Robert Louis Delapaz, Dobbs Ferry, NY (US)

(73) Assignee: Rockland Technimed Ltd., Airmont, NY (US)

( * ) Notice: Subject to any disclaimer, the term of this patent is extended or adjusted under 35 U.S.C. 154(b) by 68 days.

(21) Appl. No.: 11/250,372

(22) Filed: Oct. 17, 2005

(65) Prior Publication Data

US 2007/0086948 A1   Apr. 19, 2007

(51) Int. Cl.
  *A61B 5/055*   (2006.01)
(52) U.S. Cl. ..................................... 424/9.3
(58) Field of Classification Search .................. 424/9.3
  See application file for complete search history.

(56) References Cited

U.S. PATENT DOCUMENTS

| | | | | |
|---|---|---|---|---|
| 4,996,041 | A * | 2/1991 | Arai et al. | 424/9.37 |
| 5,339,814 | A * | 8/1994 | Lasker | 600/420 |
| 5,682,883 | A * | 11/1997 | Fiat | 600/323 |
| 6,280,383 | B1 | 8/2001 | Damadian | |
| 6,727,697 | B2 | 4/2004 | Fiat | |
| 6,792,302 | B2 * | 9/2004 | Wintermark et al. | 600/407 |

OTHER PUBLICATIONS

Heiss et al. (Stroke 2004, Supp. 1, 2671-2674).*
Warach (Stroke 2003, 24, 2533-2534).*
Arai, M.D. et al., Critical Care Medicine, vol. 17, pp. 1333-1334 (1989).
Rogers et al., "T2 Imaging using O-17 for Detection of Viability in Myocardial Infarction", International Society of Magnetic Resonance in Medicine Seventh Annual Meeting, Philadelphia, U.S.A. (May 1999).
Sobesky, M.D. et al., Stroke, vol. 36, pp. 980-985 (2005).
C.P. Derdeyn, MD, et al., "Cerebral hemodynamic impairment: Methods of measurement and association with stroke risk," Neurology, vol. 53(2), Jul. 22, 1999, pp. 251-259.
Bradley et al., "Blood flow and oxygen extraction fraction in regions of oedema following head injury", Critical Care, vol. 8, Suppl. 1, p. 311 (2004).
Study of "Measurement of Cerebral Oxygen Extraction Fraction Using MRI Technique", by Yuan-Heng Mo, M.D. (Jul. 2004).
Yamauchi et al., Journal of Neurology Neurosurgery and Psychiatry, vol. 75, pp. 33-37 (2004).
Derdeyn et al., Stroke, vol. 29, pp. 754-758 (1998).
An et al., Magnetic Resonance in Medicine, vol. 47, Issue 5, pp. 958-966 (2002).
Ansorge et al., Proc. Intl. Soc. Mag. Reson. Med., vol. 11, p. 1794 (2003).
Young et al., J. Cereb. Blood Flow Metab., vol. 16, No. 6, pp. 1176-1188 (1996).

* cited by examiner

*Primary Examiner*—Michael G. Hartley
*Assistant Examiner*—Melissa Perreira
(74) *Attorney, Agent, or Firm*—Dickstein Shapiro LLP

(57) ABSTRACT

Various pathophysiological states are determined by evaluating the rate of $^{17}O$-containing water production oxygen using proton MRI. The method can be used to identify viable but threatened myocardium, injured by viable muscle, penumbra tissue in a stroke patient, and the like.

16 Claims, No Drawings

TISSUE METABOLIC STRESS MONITORING

BACKGROUND OF THE INVENTION

One of the key items of information that physicians need to know for the selection and timing of medical treatment is the state of diseased tissue and the likelihood it will return to normal viability in response to therapy. Many methods are used to assess tissue health including the history of the patient's symptoms, physical examination, and laboratory and imaging studies of tissue biochemistry and anatomy. Abnormal anatomy, signal changes reflecting the state of tissue water and basic physiologic measurements such as water diffusion and blood flow are among the methods used. These methods are useful but are themselves secondary signs of more fundamental properties of tissue metabolism and potential. Magnetic resonance imagery (MRI) is one of the most frequently used imaging methods to assess tissue viability and although it is a highly sensitive and specific tool, it also depends primarily on secondary signs of tissue health to assess tissue viability.

The ability of MRI procedures to distinguish between sub-areas within a given tissue area is often limited. One example of this concerns the determination of penumbra in a stroke patient. The importance of this determination is apparent from the fact that there are an estimated 731,000 strokes and 4 million stroke survivors annually in the United States alone, making stroke a major cause of long-term disability. Considering also the mortality and morbidity caused from cardiac arrest, traumatic brain injury and perinatal asphyxia, it is easily understood that the economic and social burden of CNS injury is huge. Beyond the direct hospitalization and treatment costs, the indirect costs of lost productive years is of importance because ischemic stroke is prevalent in the older population and traumatic brain injury and perinatal asphyxia are diseases mainly of the young and newborns, respectively. Thus, indirect costs are even higher than direct costs for traumatic brain injury and perinatal asphyxia.

In the assessment of acute cerebral ischemic stroke (and cerebral tissue at risk for ischemic injury in chronic vascular stenosis), a key item of information needed for therapy decisions is an accurate differential identification of normal tissue, tissue injured beyond recovery (the ischemic infarct "core") and tissue at risk for permanent injury but potentially salvageable with therapy (the ischemic infarct "penumbra"). The infarct core is the zone of absent cerebral blood flow (CBF) or low CBF with tissue metabolism below a viable threshold ($CMRO_2$), usually identified on MRI as a zone of severely restricted diffusion indicating the failure of cellular energy metabolism. The penumbra, tissue that remains viable but has reduced blood flow and is at high risk of energy failure and cell death, has two zones. The region of the penumbra called the "oligemic" zone is where prolonged reduced blood flow may be compatible with tissue survival and therapy may only be needed to prevent further flow reduction. Thus, the compensation for early or mild reduced blood flow in stroke (Stage 1) takes the form of vasodilation and increased coronary blood volume which maintains blood flow sufficiently to allow normal cellular metabolism to be maintained at a normal oxygen extraction fraction (OEF). With more severe blood flow reduction (Stage II), the vasodilation capacity is exceeded, normal flow cannot be maintained and OEF is increased because more oxygen must be extracted per volume of blood to maintain normal cellular metabolism. This is the true ischemic penumbra and is also called the zone of "misery perfusion". This tissue will not survive without treatment to improve blood flow. The end point of this trend is extreme or prolonged blood flow reduction leading to failure of cellular energy metabolism, apoptosis, cell death and reduction of OEF below normal in response to the absence of oxygen demand. "Necrotic" cell death occurs because the mitochondria are incapable of maintaining ATP production with inadequate oxygen delivery. This "oxidative stress" also activates a mitochondrial trigger for "apopotic" cell death, or programmed cell death mediated by a cascade of protein activation and DNA injury. Similar principles apply to the assessment of tissue at risk in chronic vascular stenosis where elevated OEF identifies tissue at the highest risk of developing infarction.

When normal perfusion pressure is not maintained, reflex vasodilation occurs to maintain normal blood flow. This response, as well as the reflex vasoconstriction observed with increased perfusion pressure, is known as autoregulation or Stage 1 hemodynamic compromise. It maintains normal flow by reducing the vascular resistance to arterial inflow. With further reductions in perfusion pressure, the capacity of autoregulatory vasodilation to maintain normal blood flow is overcome and blood flow begins to decrease. Although the delivery of oxygen falls, the brain can increase the amount of oxygen it extracts from the blood (the oxygen extraction fraction or OEF) to maintain normal cerebral oxygen metabolism and function. This phenomenon of reduced blood flow and increased oxygen extraction is the reason for "misery perfusion" or Stage 2 hemodynamic failure. Once oxygen extraction becomes maximal, further decreases in perfusion pressure (and consequently blood flow) will lead to disruption in normal oxygen metabolism and ultimately to infarction.

At present, regional measurements of OEF can be made only with positron emission tomography (PET) using O-15 labeled radiotracers. Both absolute values and side-to-side ratios of quantitative and relative OEF have been used for the determination of abnormal from normal. MRI measurements using pulse sequences sensitive to deoxy-hemoglobin, which is increased in regions with increased oxygen extraction, are just beginning to be be developed to provide similar information.

The present invention is based on a recognition that tissue blood flow, molecular oxygen delivery, oxygen metabolic rate and oxygen extraction fraction can all be measured with a form of MRI which employs $^{17}O_2$. While all of these parameters are important for the assessment of the metabolic state of tissue, the oxygen extraction fraction (OEF) is the variable which is the most sensitive and specific for tissue in a state of "oxidative stress" and so is the key predictor of tissue viability because total oxygen consumption may appear to be constant due to the tissue's ability to compensate for locally reduced oxygen delivery. Reductions of blood flow, oxygen delivery and oxygen metabolic rate below normal levels do not specifically indicate whether the oxygen supply is deficient to tissue with normal metabolic demand (ischemia or hypoxemia) or appropriate for tissue with a reduced metabolic demand (metabolically suppressed, stunned or hibernating or dead tissue). Elevation of the OEF specifically indicates that there is a tissue metabolic demand for oxygen that is not being adequately met by the oxygen supply for the blood. More precisely, there is an increased gradient along which oxygen is diffusing between the higher concentration in blood and the lower concentration in tissue, produced by the rate of oxygen consumption in tissue mitochondria. This increased concentration gradient induces a greater percentage of blood oxygen to be released from hemoglobin and transported to the tissue. OEF is not elevated, but is reduced in metabolically suppressed or dead tissue because the blood-tissue oxygen concentration gradient is minimized. The prediction of tissue viability by OEF is based on the frequent observation that substantial, prolonged OEF elevation directly precedes cell death in a variety of tissues. The oxidative stress indicated by elevated OEF leads to cell death by necrosis from mitochondrial energy depletion (failure of ATP production) and/or mitochondrial triggering of the molecular cascade leading to apoptosis, or "programmed cell death".

The quantitative measure of oxygen removal from blood, the oxygen extraction fraction (OEF), is the percent of oxygen removed per unit volume of blood, caused by oxygen diffusion along the gradient from the high concentration in the blood to the low concentration in the metabolizing tissue. Normal brain tissue OEF is approximately 40% and may be as high as 60-70% in the subarea of penumbra misery perfusion. In acute ischemia, tissue with elevated OEF is likely to progress to cell death unless normal blood flow is restored (e.g. by thrombolysis) or metabolic demand is reduced (e.g. by hypothermia). In transient ischemic attack (TIA) or chronic vascular stenosis, tissue with elevated OEF is at risk for permanent injury if blood flow is reduced below the marginal level maintaining tissue viability.

It is important to initiate acute therapy promptly to prevent penumbra tissue from progressing to infarction and thereby preserve, at least to some degree, the normal functioning of this brain tissue. These acute therapies have no effect on the ischemic core or infarction but involves a high degree of risk. For example, anti-coagulant therapy can be dangerous to the patient in that normal coagulation is suppressed. Because of the possible adverse effects, the treating physician must evaluate the risks and benefits of the therapy, an evaluation which includes consideration of the likelihood of converting the penumbra tissue into "normal" tissue. This requires estimating how much true ischemic penumbra tissue exists.

In the absence of other factors, one of the principle items of information on which the treating physician makes an evaluation of the risk and benefits is the amount of time since the stroke apparently occurred. Since the progression from penumbra to infarction is relatively rapid, usually measured in terms of hours, and there is a lack of precession about when the cerebral schema event commenced, the treating physician is essentially forced to make a risk/benefit evaluation based on the limited information which may be available. A diagnostic procedure which will assist the physician in making an evaluation is clearly desirable. Positron emission tomography (PET) has been found to provide detailed insight into the changes which occur after a cerebral ischemia. PET detects viable but hyperperfused tissue that is characterized by an elevated OEF and accessible to acute therapy. It is thus capable of providing a relatively accurate identification of the true ischemic penumbra tissue. However, PET involves the use of a radioactive isotope of oxygen, $^{15}O$, and a substantial radiation dose. Consequently, the substitution of data from stroke magnetic resonance imagery induced markers has been recognized as desirable. But stroke MRI induced markers for tissue integrity or cerebral profusion do not satisfactorily identify the penumbra.

Currently, the most frequently used MRI methods for evaluating the health of brain tissue and the risk of infarction are bolus-contrast perfusion-weighted imaging (PWI) and diffusion-weighted imaging (DWI). PWI is performed by injecting a rapid bolus of gadolinium-chelate contrast agent intravenously while monitoring its passage through the brain circulation with rapid MR imaging, at approximately 1 image per second. Spatial maps of cerebral blood volume (CBV), tissue circulation mean transit time (MTT) and cerebral blood flow (CBF) are calculated using the central volume principle. These maps are compared to the diffusion weighted images which show infarcted tissue as high signal, representing restricted diffusion in cells that have undergone complete failure of energy metabolism. When this comparison shows areas of reduced perfusion outside the restricted diffusion infarction, a PWI-DWI "mismatch" is present and is considered a surrogate marker of the metabolic penumbra.

The major limitation of the PWI-DWI mismatch assessment of tissue at risk is that it is based on indirect measures of the tissue metabolic status. The practical effect of this limitation was studied in order to evaluate the accuracy of using mismatch to indicate penumbra and the study found that mismatch overestimated the volume of penumbra, and therefore the tissue at risk which was subject to acute therapy. See Sobesky et. al., Does the Mismatch Match the Penumbra?, Stroke, 2005; 36:980-985. Accordingly, mismatch as determined by MRI procedures provides inaccurate information to the treating physician. But an MRI procedure has the advantages over PET of an absence of ionizing radiation exposure to the patient and medical personnel, and the absence of a need for an expensive, complex, on-site cyclotron and radiation chemistry lab. An MRI procedure which more accurately identifies penumbra information for the treating physician that mismatch is clearly desirable.

The present invention is based, in part, on the recognition that the mismatch zone includes a mix of tissue with reduced flow and normal OEF ("oligemic" perfusion) and tissue with elevated OEF ("misery" perfusion). In the oligemic perfusion zone, cellular oxygen demand is close to the oxygen level supplied by blood flow and the tissue is likely to remain viable with continued low perfusion. In the misery perfusion zone, cellular oxygen demand is well above the oxygen level supplied by blood and the tissue is likely to progress to infarction unless perfusion is improved or returned to normal. It is also based, in part, on the recognition that the PET analysis is not effected by the oxygen uptake compensation by the tissue in the same way that MRI mismatch analysis is effected. It also takes advantage of the stable nature of the $^{17}O_2$ isotope compared to the 2 minute half-life decay of $^{15}O_2$ which will allow distribution of an $^{17}O_2$ viability agent in an "off the shelf" form to the large installed base of MRI scanners now in operation.

It is the object of this invention to provide a new method for differentiating or monitoring tissue response to stress, such as for instance, determining penumbra brain tissue in a stroke patient, using proton magnetic resonance imaging. This and other objects of the invention will become apparent from the following detailed description.

SUMMARY OF THE INVENTION

The differentiating and/or monitoring of tissue response to stress is determined by measuring the rates of production of $H_2^{17}O$ in a plurality of zones of the tissue of interest in a patient by means of proton magnetic resonance imaging after the patient has had administered an effective amount of a diagnostic imaging agent based on oxygen-17. The rates of production between the various zones of a given tissue area in which there is production are compared and the zone(s) in which the rate of production is greater than other zones is identified.

One practical application of the method of the invention involves determining the existence of and/or the extent of penumbra brain tissue in a stroke patient by measuring the rates of production of $H_2^{17}O$ in a plurality of zones of the brain of the patient by means of proton magnetic resonance imaging after the patient has had administered an effective amount of a diagnostic imaging agent based on oxygen-17.

The rates of production between the various zones in which there is production are compared and the zone(s) in which the rate of production is greater than other zones is reflective of the penumbra tissue.

MRI methods for the quantitative detection of $^{17}O_2$ and $H_2^{17}O$ in tissue have been developed over the last 20 years and permit the in vivo quantitative determination of molecular oxygen concentration, oxygen extraction fraction, oxygen metabolism and blood flow. An improved method which involves introducing oxygen-17 into tissues for imaging is described in U.S. Pat. No. 4,996,041. After the oxygen-17 is absorbed by the cell, it is converted into water. Since the non-radioactive isotope oxygen in the water perturbs the proton signal, it creates a negative contrast on the MRI scan. It has now been recognized that this allows zones of tissue to be identified as a result of different rates of oxygen uptake by the cells. It is known that oxygen starved hypotoxic tissue consumes a larger percentage of oxygen than normal tissue whereas nonviable or necrotic tissue does not take up the oxygen and does not produce any water. This has permitted nonviable tissue, normal tissue and oxygen starved hypoxic tissue to be distinguished. However, the gross oxygen uptake in normal tissue and stressed tissue such as penumbra tissue is often approximately the same. It has now been recognized that the oxygen uptake is not uniform throughout the stressed tissue, with some parts having less oxygen uptake than normal tissue while other parts have more oxygen uptake. For example, the penumbra tissue as a whole is not oxygen starved, in that portions of that tissue are compensating for other portions, taking up more oxygen and producing water at a greater rate so that the gross oxygen uptake and gross water production is approximately that of normal tissue. Nevertheless, the fact that the rate of water production is greater allows the penumbra tissue to be distinguished from normal tissue. Similarly, a differential rate of water production allows pathophysiological states resulting from stress (e.g., disease, therapy) to be identified and/or quantified in tissue zones where the water production over a larger area normally appears to be uniform.

DESCRIPTION OF THE INVENTION

In accordance with the present invention, the rate of production of $H_2^{17}O$ in a plurality of zones of tissue, such as the brain of a stroke patient, is measured by means of proton magnetic resonance after administering an effective imaging amount of a diagnostic imaging agent comprised of a complex of oxygen-17. Nonviable tissue does not produce water, and this allows, in accordance with prior practice, viable and nonviable tissue to be distinguished. The present invention looks to the rates of water production in a plurality of zones in the area in which there is production and comparison allows the zones to be distinguished. This provides information about the effect and effectiveness of therapy to restore viability, tissue regeneration, and the like. In the case of stroke patients, the zone(s) which has a greater rate of production than other zones is considered to define the penumbra and this method allows the size of the penumbra brain tissue to be more accurately identified than through "mismatch".

The use of proton magnetic resonance imaging after administrating an effective imaging amount of a diagnostic imaging agent comprising a complex of oxygen-17 is known and is described, e.g., in U.S. Pat. No. 4,996,041, the disclosure of which is hereby incorporated by reference. Briefly, the imaging agent is preferably comprised of a complex of the non-radioactive isotope oxygen-17, a biologically acceptable liquid carrier, and possibly a biologically acceptable emulsifying agent, the complex having an ionic composition essentially equal to that of blood and having an average particle size of less than about 0.6 microns.

Oxygen-17 is a commercially available oxygen isotope and can be obtained from several sources. The biologically acceptable liquid carrier can be a perflorinated compound such as, for example, perfluorotibutylamine, perfluorobutyltetrahydrofuran, perfluoropolyether, and the like, although it is possible to use other liquids including blood or blood plasma or modified hemoglobin compounds. The liquid carrier generally constitutes about 5 to 50% by weight, and more preferably from about 15 to 30% by weight, of the composition. In some instances, the composition will contain a nontoxic, biologically acceptable, emulsifying agent or surfactant which is compatible with both the oxygen-17 and the carrier liquid, and has no adverse effects on the body. A preferred surfactant is a polyoxyethylene-polyoxypropylene copolymer. The surfactant, when present, is generally about 1 to 20%, more preferably about 2.5 to 10%, in an aqueous solution with an ionic composition resembling that of blood, based on the total weight of the diagnostic agent.

In general, the ratio of oxygen-17 to the carrier liquid and the emulsifying agent (if present) will usually be about at least about 1:5 and generally up to about 1:4.

Administration of the diagnostic agent is preferably carried out by intravenous profusion. A wide variety of methods and instrumentation can be employed to introduce the agent into the body of the subject being examined. A preferred method is to use a catheter so that the agent can be directed to a desired site in the body and greater control can be obtained of the amount introduced to provide the desired imaging. The catheter also makes it possible to administer therapeutic agents after or during the imaging procedure. The complex employed will be an effective amount necessary to provide the desired imaging and this can vary from a few milliliters to 10 milliliters or more.

An advantage of the use of this imaging agent is that it can be detected using commercially available magnetic resonance equipment with little or no modification. Commercially available MRI units can be characterized by the magnetic field strength used, with a field strength of 3.0 Tesla being the current maximum and 0.2 Tesla being the current minimum. For a given field strength, each nucleus has a characteristic frequency and moreover, the imaging of elements can be conducted simultaneously or sequentially.

Further information about the use of oxygen-17 in MRI can be found in the aforementioned U.S. Pat. No. 4,996,041.

The following example is illustrative of the invention.

A complex was prepared by deoxygenation of natural oxygen (oxygen-16) from a mixture of perfluorotributylamine (PFC) and a polyoxyethylene-polyoxypropylene emulsifying agent obtained from the Green Cross Corporation of Osaka, Japan. The mixture was sparged with nitrogen and warmed to remove the oxygen-16. Thereafter, the mixture was contacted with an equal volume of 70% oxygen-17 gas and mixed well to insure absorption of the gas. The resulting mixture consisted of 100 ml of complex and was kept under cooling conditions.

A dog (body weight 5 kg) was anesthetized with pentabarbital (30 mg/kg). A cannula was inserted into a femoral vein to an interior vena cava for saline infusion (10 ml/kg/hr) and later infusion of the (oxygen-17-PFC complex). The dog was fixed on the platform and positioned in the knee coil under the GE 1.5 Tesla Sigma Imaging system (1H resonant frequency, 63.9 Mhz). A control image was obtained with the infusion system in place. The dog brain was scanned before (control), during, and after infusion of the complex and 5 mm thick axial images at different locations (multislice) of the brain tissue were obtained. The images were reconstructed using 2 DFT of two exitations of 256 data lines and magnitude reconstruction.

After getting the control image of the brain, the complex was infused through the cannula at a constant rate (100 ml/8 min). During and after the infusion, the dog brain was scanned at different locations, and several sets of images were obtained over a two hour period.

Compared to the control image, the $T_2$-weighted images exhibited considerable decrease (32-40%) in proton intensity. This effect was not transitory but persisted for at least 2 hours, and thought to be due to the paramagnatic effect of oxygen-17 derived from $H_2^{17}O$ as a metabolite of the complex on the proton the $T_2$-weighted image. $T_1$-weighted images did not show any changes in the proton image intensities as compared to the $T_1$ control image. It was therefore evident from the data obtained, that on administration of the complex of the present invention to the target site, in vivo detection of the $H_2^{17}O$ tissue metabolite as one of the metabolized by products is demonstrable by proton NMR imaging. The ability to detect the rate of $H_2^{17}O$ formation in different tissue areas is also confirmed.

The process when employed in connection with an individual suspected of having had a stroke is preferably practiced by drawing an aliquot of the patient's blood, mixing it with $^{17}O_2$, and then reinjecting the resulting $^{17}O_2$ containing blood back into the patient. Proton MRI is then effected and the rate of $H_2^{17}O$ production determined. This same procedure can also be used when evaluating the in vivo tissue response of to regeneration and apoptosis, in various therapies such as gene or physical therapy, exercise, and the like.

The various embodiments described herein were for illustrative purposes only and were not intended to limit the invention. Various changes and modifications can be made without departing from the spirit and scope of the invention.

For instance, the invention's use of OEF monitoring is also applicable in the non-acute setting of brain tissue that is chronically "oxygen starved" distal to a vascular stenosis. This has been studied extensively with $^{15}O_2$ PET which clearly indicates a unique role for measurement of OEF as the key indicator of tissue at risk of ischemic injury and the importance of this information for therapeutic decision-making. Brain tissue in the stenotic vessel territory (e.g. the cerebral hemisphere distal to an internal carotid artery or lobe distal to a middle cerebral artery stenosis) is at greater risk of developing an ischemic infarct with prolonged low flow or minor reduction in flow when the OEF is elevated to indicate a state of "misery perfusion". The treating physician will use this information to determine the need and urgency of procedures that correct the stenosis (e.g. endarterectomy, angioplasty or stent) or provide alternate blood flow supply routes (e.g. EC-IC bypass).

MRI $^{17}O_2$ OEF in accordance with the present invention can play a major role in the evaluation of cerebral transient ischemic attacks (TIA) which are precursors of ischemic stroke in as much as 30% of cases but are currently diagnosed with low specificity by clinical history and neurological examination. A variety of conditions may mimic TIA such as seizure or transient hypoglycemia. This imprecision in the clinical diagnosis of TIA has made research trials into drugs that may prevent subsequent ischemic stroke very difficult to design and validate. Highly consistent data sets of true TIA's cannot be obtained and treatment outcome data is always questioned on the basis of non-specificity to the presumed tissue pathology (transient tissue ischemia). Currently these types of drug research studies depend on a positive diffusion-weighted MRI to "confirm" the occurrence of ischemia by showing restricted diffusion in injured tissue. Unfortunately, this time point is too far along in the pathologic process and really identifies patients with small, potentially reversible, ischemic strokes, rather than those without injury at risk for major stroke. MRI $^{17}O_2$ OEF can provide the needed measure of risk of ischemic tissue injury before actual injury occurs. This allows drug testing to more specifically target the relevant pathologic process and more precisely time therapy for maximum benefit. Analogously, MRI $^{17}O_2$ OEF can be applied to the similarly difficult diagnosis of cardiac ischemic disease by subjective clinical symptoms of chest pain and angina. MRI $^{17}O_2$ OEF can be used to improve the spatial and temporal targeting of drug or interventional therapies to the early, pre-injury stage of the cardiac ischemia disease process. These are illustrative examples of the use of MRI $^{17}O_2$ OEF as a surrogate marker for pathology that can be used in drug discovery and testing that are likely to improve the precision of drug testing and decrease drug development costs substantially.

In the heart and coronary vessels, acute vascular occlusions and chronic stenoses produce analogous metabolic scenarios to those described in the brain above. Elevated OEF in cardiac muscle distal to acute thrombosis or a chronic stenosis is an indicator of unmet oxidative metabolic demand and therefore elevated risk of necrotic and/or apoptotic cell death. OEF elevations support decisions to perform emergency interventional thrombectomy and/or thrombolysis in the acute situation and elective angioplasty and stenting in the chronic situation.

MRI $^{17}O_2$ OEF measurement of oxidative stress may also be applied to monitor the viability of transplanted tissue and organs. Elevated MRI $^{17}O_2$ OEF is an indicatation of an elevated risk of transplant failure, allowing prompt measures to improve the organ blood supply (e.g. renal transplant) or treat inflammatory or immune reactions that may be causing microvascular ischemic injury to the transplanted tissue.

MRI $^{17}O_2$ OEF can also be an indicator of tissue with growing oxidative metabolic demand that is outstripping its blood supply—e.g. growing neoplasm which is "ahead" of its VegF induced angiogenesis. Other examples of MRI $^{17}O_2$ OEF as a measure of unmet oxidative metabolic demand in growing tissue are regenerating tissue (e.g. liver), biomedically engineered tissue (e.g. tissue culture skin grafts) or genetically engineered tissue regeneration. A situation similar to growing tissue occurs in exercising muscle which is being pushed into the "anaerobic" zone and outstripping its blood oxygen supply (inducing increased vascular capacity over time in response to training—probably closely linked to the production of lactate through anaerobic glycolysis when inadequate oxygen is available). This can have broad application to exercise physiology, sports medicine and equine veterinary medicine with broad economic implications.

Cardiac, visceral, transplant and other tissues also can also have portions of the areas visualized by MRI which differ from one another. The process of cellular respiration is identical in all tissue and the compensation during metabolic stress is similar albeit the metabolic activity among different tissue types varies based on their function. This means that an ability to differentiate subareas of tissue by means of MRI for the evaluation of the reaction to stress has a wide application and is not limited to the evaluation of cerebral tissue.

What is claimed is:

1. A method of differentiating zones in ischemic tissue by measuring an oxygen extraction fraction in the ischemic tissue by means of a proton magnetic resonance imaging system, the method comprising:

administering an effective imaging amount of a diagnostic imaging agent, the diagnostic imaging agent comprising $^{17}O_2$ and a biologically acceptable carrier, wherein said diagnostic imaging agent has an ionic composition essentially equal to that of blood and an average particle size of less than about 0.6 microns; and determining a risk of tissue damage by comparing a first oxygen extraction fraction of a first tissue zone in the ischemic tissue to a second oxygen extraction fraction of a second tissue zone in the ischemic tissue using the proton magnetic resonance imaging system.

2. The method of claim 1 in which the biologically acceptable carrier comprises blood.

3. The method of claim 2 in which the diagnostic imaging agent further comprises an emulsifying agent.

4. The method of claim 3 in which the first oxygen extraction fraction of the first tissue zone is quantified relative to the second oxygen extraction fraction of the second tissue zone.

5. The method of claim 1 in which the diagnostic imaging agent further comprises an emulsifying agent.

6. The method of claim 5 in which the first oxygen extraction fraction of the first tissue zone is quantified relative to the second oxygen extraction fraction of the second tissue zone.

7. The method of claim 1 in which the first oxygen extraction fraction of the first tissue zone is quantified relative to the second oxygen extraction fraction of the second tissue zone, one of the first and second tissue zones being normal tissue.

8. A method of determining penumbra brain tissue in a stroke patient by measuring an oxygen extraction fraction in the brain by means of a proton magnetic resonance imaging system, the method comprising:

administering an effective imaging amount of a diagnostic imaging agent, the diagnostic imaging agent comprising a complex of $^{17}O_2$ and a biologically acceptable liquid carrier, wherein said complex has an ionic composition essentially equal to that of blood and an average particle size of less than about 0.6 microns; and identifying tissue under oxidative stress, said identifying comprising comparing an oxygen extraction fraction from a first tissue zone in the penumbra to an oxygen extraction fraction of a second tissue zone in the penumbra using a proton magnetic resonance imaging system.

9. The method of claim 8 in which the biologically acceptable liquid carrier comprises blood.

10. The method of claim 9 in which the diagnostic imaging agent further comprises an emulsifying agent.

11. The method of claim 10 in which the first oxygen extraction fraction of the first tissue zone is quantified relative to the second oxygen extraction fraction of the second tissue zone.

12. The method of claim 8 in which the diagnostic imaging agent further comprises an emulsifying agent.

13. The method of claim 12 in which the first oxygen extraction fraction of the first tissue zone is quantified relative to the second oxygen extraction fraction of the second tissue zone.

14. The method of claim 8 in which the first oxygen extraction fraction of the first tissue zone is quantified relative to the second oxygen extraction fraction of the second tissue zone.

15. The method of claim 8 further comprising:

comparing the oxygen extraction fraction in a third tissue zone in normal brain tissue to the oxygen extraction fraction in the first tissue zone and the second tissue zone by means of the proton magnetic resonance imaging system; and quantifying the oxygen extraction fraction of the third tissue zone relative to the oxygen extraction fraction of the first tissue zone and the second tissue zone.

16. The method of claim 1 further comprising:

comparing the oxygen extraction fraction in a third tissue zone in normal tissue to the oxygen extraction fraction in the first tissue zone and the second tissue zone by means of the proton magnetic resonance imaging system; and quantifying the oxygen extraction fraction of the third zone relative to the oxygen extraction fraction of the first zone and the second zone.

\* \* \* \* \*